United States Patent [19]

Berlin

[11] Patent Number: 4,974,594
[45] Date of Patent: * Dec. 4, 1990

[54] BIOMEDICAL ELECTRODE AND REMOVABLE ELECTRICAL CONNECTOR

[75] Inventor: Lee M. Berlin, Minnetonka, Minn.

[73] Assignee: Lec Tec Corporation, Minnetonka, Minn.

[*] Notice: The portion of the term of this patent subsequent to Mar. 27, 2007 has been disclaimed.

[21] Appl. No.: 445,439

[22] Filed: Dec. 4, 1989

Related U.S. Application Data

[63] Continuation of Ser. No. 7,325,927, Mar. 20, 1989, Pat. No. 4,911,657.

[51] Int. Cl.⁵ ............................................. A61B 5/402
[52] U.S. Cl. ................................... 128/640; 128/798; 439/258; 439/346; 439/502; 439/729; 439/889; 439/909
[58] Field of Search ............... 128/640, 641, 798, 802, 128/803; 606/32; 439/142, 166, 258, 346, 371, 451, 502, 506, 729, 859, 868, 887, 889, 909

[56] References Cited

U.S. PATENT DOCUMENTS

| | | |
|---|---|---|
| 2,943,627 | 7/1960 | Howell .................. 128/416 |
| 3,720,209 | 3/1973 | Boldue .................. 128/2.06 E |
| 3,911,906 | 10/1975 | Reinhold, Jr. ......... 128/2.06 E |
| 4,072,388 | 2/1978 | Dunn .................. 128/641 X |
| 4,112,941 | 9/1978 | Larimore ............. 128/2.06 E |
| 4,126,126 | 11/1978 | Bore et al. ........... 439/909 |
| 4,166,465 | 9/1979 | Esty et al. ........... 606/32 |
| 4,239,046 | 12/1980 | Ong .................... 128/640 |
| 4,273,135 | 6/1981 | Lavimore ............. 128/640 |
| 4,522,211 | 6/1985 | Bare et al. ........... 128/640 |
| 4,635,642 | 1/1987 | Cartmell et al. ..... 128/640 X |
| 4,671,591 | 6/1987 | Archer ................ 439/346 |
| 4,674,512 | 6/1987 | Rolfe .................. 128/640 |
| 4,685,467 | 8/1987 | Cartmell et al. ..... 128/640 |
| 4,702,256 | 10/1987 | Robinson et al. ..... 439/729 |
| 4,706,680 | 11/1987 | Keusoch et al. ...... 128/640 |
| 4,731,032 | 3/1988 | Noorily ............... 439/142 |
| 4,797,129 | 1/1989 | Malana ................ 439/729 |
| 4,798,208 | 1/1989 | Foasse, Jr. .......... 128/640 |
| 4,911,657 | 3/1990 | Berlin ................. 128/640 X |

FOREIGN PATENT DOCUMENTS 675494 12/1963 Canada .
2159639 7/1987 Japan .................... 128/641

*Primary Examiner*—Lee S. Cohen
*Attorney, Agent, or Firm*—James V. Harmon

[57] ABSTRACT

A biomedical "tab" type of electrode suited for use with male and female connectors of the type that are adapted to snap together is provided. The female connector is located at one end of a lead wire. A male snap connector is secured to the lead wire by means of a flexible tether. The electrode includes an extension or tab having an opening therein. The tether is mounted on the lead wire and is preferably adapted to slide along its length. During use, the male snap connector can be moved into proximity of the female connector and aligned with it on opposite sides of the tab portion of the electrode and then brought into contact and connected to each other through the opening in the tab to establish both a mechanical and an electrical connection with the tab of the electrode.

7 Claims, 2 Drawing Sheets

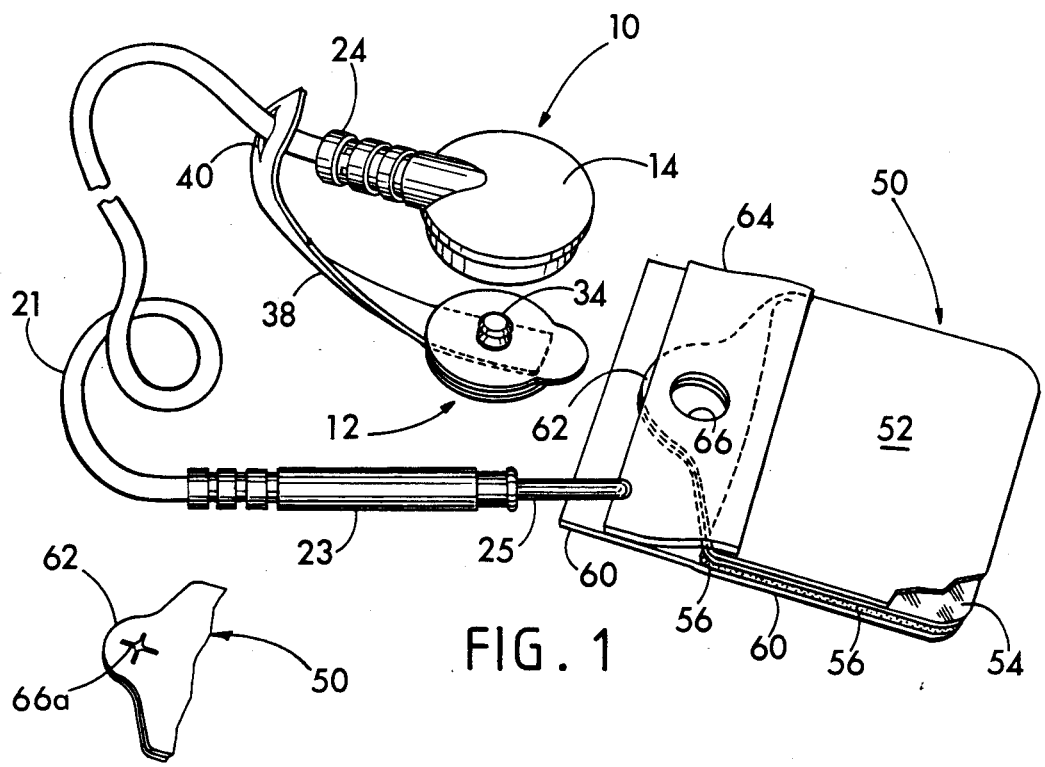
FIG. 1
FIG. 1a
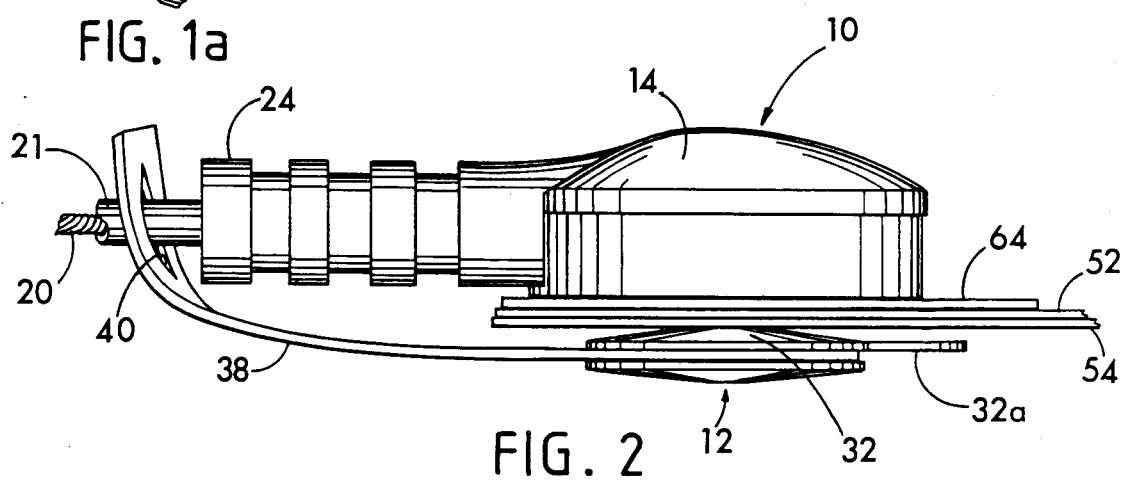
FIG. 2
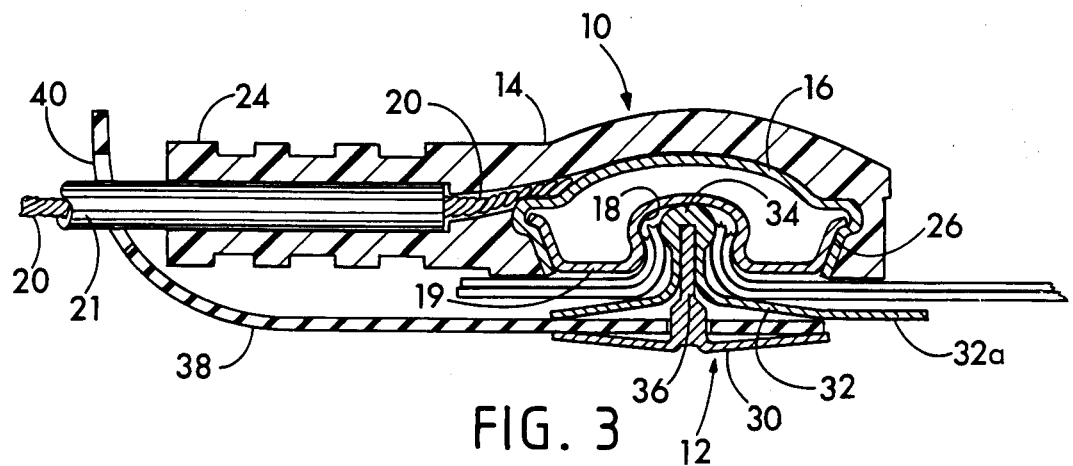
FIG. 3

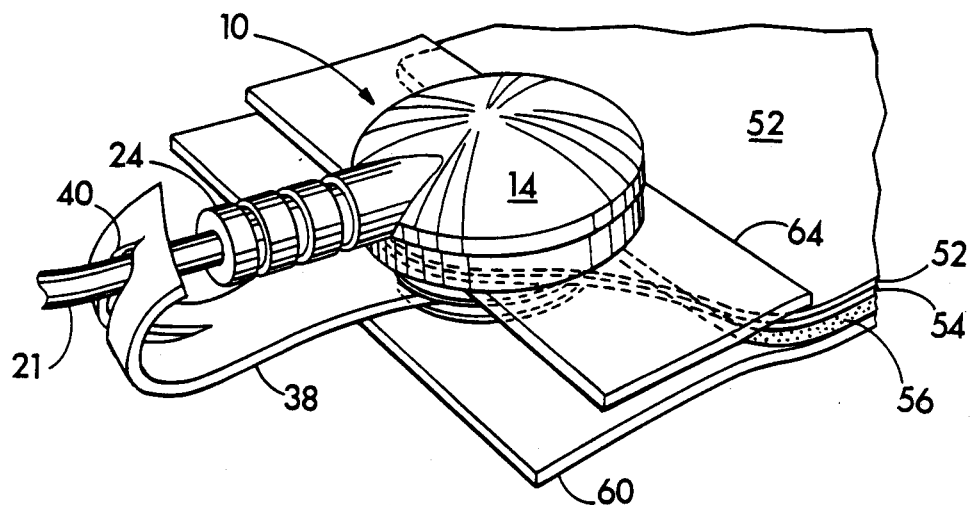
FIG. 4
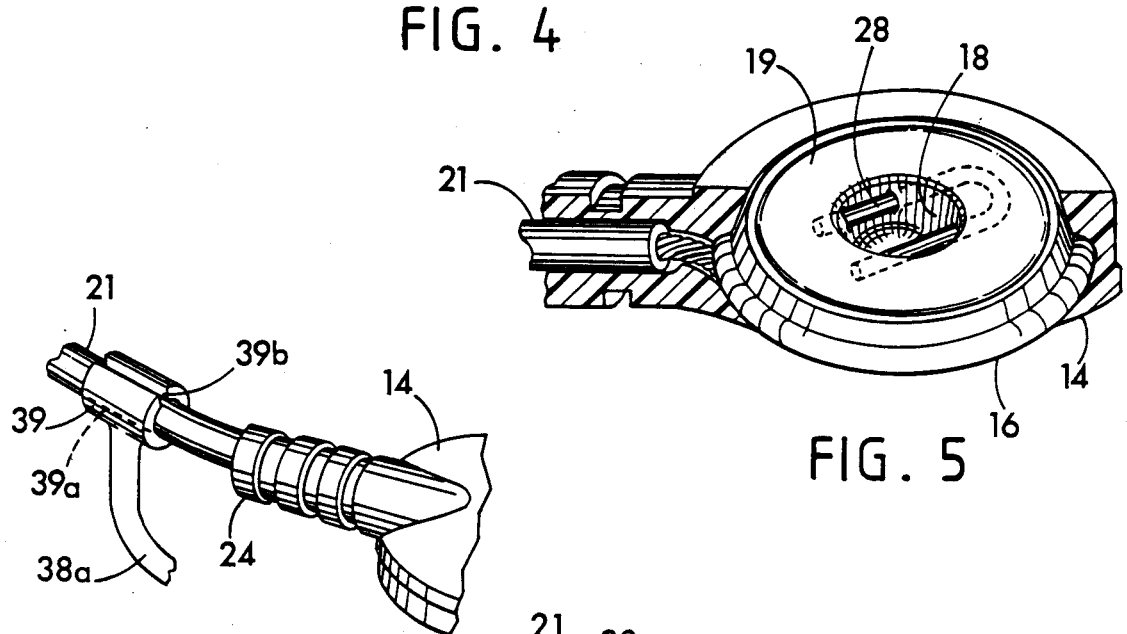
FIG. 5
FIG. 6
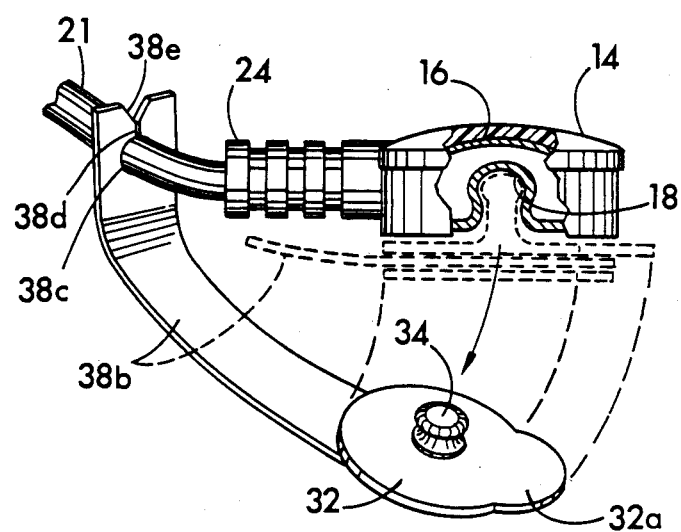
FIG. 7

BIOMEDICAL ELECTRODE AND REMOVABLE ELECTRICAL CONNECTOR

This is a Continuation-in-Part of application Ser. No. 07/325,927 filed Mar. 20, 1989, now U.S. Pat. No. 4,911,657.

FIELD OF THE INVENTION

The present invention relates to biomedical devices and more particularly to biomedical electrodes of the kind that are attached to the body for monitoring or stimulation purposes

BACKGROUND OF THE INVENTION

Two types of biomedical electrodes are used primarily in hospitals for EKG work. Both include a conductive backing laminated to a flexible electrically conductive gel matrix that is applied to the skin of a patient. In one type, a male snap connector is fastened to the backing. During use, a female snap connector at one end of a lead wire is snapped onto the male connector to make electrical contact with the electrode. The other type of electrode has no snap connector and is therefore substantially less expensive. Instead, it has a lateral extension or tab on one side or at the center to which an alligator clip can be fastened as described in U.S. Pat. Nos. 4,674,512 and 4,798,208. The problem with the second type, which will be referred to for convenience as a "tab" electrode, is that it cannot be readily connected to a female snap connector of the type in widespread use for making contact with the snap-type electrodes. As a result, many hospitals and clinics cannot benefit from the cost savings provided by the tab electrodes. Moreover, alligator clip connectors sometimes slip off and are therefore not entirely satisfactory under certain circumstances.

In view of these and other deficiencies of the prior art, it is a general objective of the invention to provide an improved means for using a female snap connector to make electrical contact with a tab electrode that has no male counterpart to the female snap connector, i.e. no male stud. Another object is to enable a lead wire provided with the female snap connector to be used with tab-type electrodes. A further object is to provide a means that allows existing snap-type leads to be reliably connected to a tab electrode or, on other occasions, to be connected in the usual way to a snap-type electrode so that it is not necessary to change leads when making a change from a snap electrode to a tab electrode.

These and other more detailed and specific objectives of the invention will be better understood by reference to the following detailed description an figures which illustrate by way of example but a few of the various forms of the invention within the scope of the appended claims

SUMMARY OF THE INVENTION

The present invention provides a biomedical "tab" type electrode especially suited for use with a pair of connectors. A lead wire has a female snap connector at one end thereof. A male snap connector is secured to the lead wire by means of a flexible tether. The electrode includes an extension or tab having an opening therein. The tether is mounted on the lead wire and is preferably adapted to slide along its length. During use, the male snap connector can be moved into proximity of the female connector and aligned with it on opposite sides of the tab portion of the electrode and then brought into contact and connected to each other through the opening in the tab to establish both a mechanical and an electrical connection with the tab of the electrode.

THE FIGURES

FIG. 1 is a perspective view of the invention just before being attached to a connector.

FIG. 1a shows a modified form of electrode.

FIG. 2 is a side elevational view of the connector assembly of FIG. 1 on a larger scale after a connection with the electrode has been made.

FIG. 3 is a vertical sectional view of FIG. 2.

FIG. 4 is a perspective view of the connector assembly in place on an electrode.

FIG. 5 is a bottom view of the female portion of the connector partly in section.

FIG. 6 is a partial perspective view of a modified form connector.

FIG. 7 is a partial perspective view of yet another form of connector.

DETAILED DESCRIPTION OF THE INVENTION

Shown in the figures is a female snap connector 10 to be used in conjunction with a tethered male snap connector 12. The female snap connector 10 includes an electrically nonconductive casing 14, e.g. a plastic sheath, within which is a metal connector body 16 having a recess or female receptacle 18 that opens downwardly as seen in the figures. Connected to the body 16 is a conductor 20 having an insulated covering 21. At the other end of conductor 20 is a plug 23 with a plug pin 25 which during use is inserted into monitoring or stimulation equipment (not shown).

Casing 14 includes an extension 24 that surrounds the insulated conductor 20 where it enters the female snap connector 10. The connector body 16 is typically hollow and is formed from cup-shaped sheet metal components, the upper one of which is press-fitted at 26 around a lower component 19 that contains the female receptacle 18 at its center. To hold the male snap connector 12 in place, the receptacle 18 can be provided with a spring such as a hairpin spring 28 for that purpose.

The snap connector 12 includes an upper stud portion 34 and a lower eyelet portion 30. The eyelet portion 30 includes a central pin 36 which projects axially through the center of the stud 34 for holding the connector 12 together by friction. It will be seen that the stud 34 includes a horizontal stud plate 32 with an extension or tongue 32a which serves as a lifting device for removing the male snap connector 12 from the female snap connector 10 by finger pressure.

A flexible tether 38 is connected to the male snap connector 12. Flexible tether 38 can be formed from a suitable flexible material such as leather, plastic, rubber and the like, plastic sheet material being preferred. Thus, the tether 38 is mounted by placing its right end over the pin 36. The stud 34 and stud plate 32 are then forced downwardly over the pin, securely locking the right end of the tether 38 in place between the stud plate 32 and the pin plate 30. At the left end of the tether 38 is an opening 40 through which the insulated conductor 20, i.e. lead wire, extends. In this way, the tethered snap connector 12 is removably mounted on the lead wire and is preferably slidable thereon. The tether 38 can be easily mounted on an existing female snap connector 10 and its lead wire 20, or removed and replaced whenever required Usually, once the tether 38 is mounted on a lead wire it is kept there indefinitely, but when not needed for use with a tab electrode, it can be slid back on the wire where it will be out of the way.

Also shown in the figures is a flexible biomedical electrode 50 which includes a flexible backing composed of two flexible sheets, including an upper electrically insulating sheet 52, e.g. a thin sheet of vinyl plastic, and an electrically conductive layer 54, e.g. a layer of tin or aluminum foil To the lower surface of conductive layer 54 is laminated a flexible layer of an electrically conductive gel matrix 56 which during use makes electrical contact with the skin of the patient The matrix 56, which is usually sticky, is covered prior to use with a removable cover sheet 60. Extending to the left, as seen in the figures, is a tab 62 composed of the layers 52 and 54. If desired, there can be applied over the left end portion of the electrode 50 an optional reinforcing tape 64 which in large part covers the tab 62. The reinforcing tape can be used to help support and strengthen the tab 62 and to make possible a more secure connection with the snap connector 10, 12. The gel matrix 56 does not cover the lower surface of tab 62. A punched opening 66 is provided in the center of the tab 62 and tape 64 when present. In this case, the stud 34 of the male snap connector 12 is simply placed through opening 66 prior to being snapped into the female receptacle 18 of the female snap connector 10. However, as shown in FIG. 3, in the event that the tab, 62 does not have a punched opening 66 the stud 34, upon being pressed upwardly into the female receptacle 18, will puncture the tab as shown in the figure, thereby forming a secure snap connection. As shown in FIG. 1a, an opening 66 in the tab 62 can comprise two cuts to provide an X configuration. The opening 66a extends all the way through the tab 62 from its top surface to its bottom surface.

Refer now to FIG. 6 which illustrates a modified form of tether wherein the same numerals refer to corresponding parts already described. Shown in FIG. 6 is a flexible tether 38a formed from plastic which in this case rather than being a flat sheet is circular in cross-section. The tether 38a has an enlarged head or collar 39 within which is provided an opening 39a communicating with a slot 39b. To mount the collar 39 over the lead wire 20, the slot 39b is spread temporarily, allowing the collar 39 to be forced onto the insulated lead wire, whereupon the collar will spring back into position as shown in the figure to hold the tether 38a in place.

Refer now to FIG. 7. In this case the tether 38b comprises a flat sheet of flexible plastic material which can have a degree of stiffness. For example, 30 mil polyethylene plastic sheet can be used. At the left end of the tether 38b is an opening 38c adapted to form a sliding fit over the insulation 21 of the lead wire 20. The opening 38c of the tether 38b has connected to it a slot 38d which is widened at its outer end 38e to make it easier to force the lead wire into the opening 38c. The tether in both FIGS. 6 and 7 can be removed by forcefully pulling it off or, if desired, by sliding it the entire length of the lead wire.

The invention is convenient to use and enables a conventional female snap connector to be connected to both snap-type and snapless tab electrodes. It provides a more secure connection than an alligator clip to a tab type electrode and enables the less expensive tab type electrodes to be used in a variety of circumstances where heretofore only the snap type electrodes could be used. Moreover, the present invention allows greater flexibility in the sense that either snap type or tab electrodes can be used with the same kind of lead wire. The invention is simple in design, rugged in construction and more reliable in operation. Unlike an alligator clip, a snap connector when secured to a tab electrode of the type described cannot be removed by tugging on the lead wire.

Many variations of the present invention within the scope of the appended claims will be apparent to those skilled in the art once the principles described herein are understood.

What is claimed is:

1. A biomedical electrode and removable electrical connector including male and female connector units adapted to be removably connected together and a lead wire to one of the connector units, said electrode comprising, an upper electrically insulating sheet, a lower electrically conductive backing in sheet form comprising a sheet of metal foil bonded to a lower surface of the insulating sheet and a flexible electrically conductive hydrogel matrix connected to a lower surface of the metal foil sheet and adapted to make electrically conductive contact with the skin and to conform to the body contours, a tab having a top and bottom surface and comprising superimposed layers of the insulating sheet and the foil sheet with coextensive edges, said tab having an opening therethrough from said top surface to said bottom surface such that the foil sheet surrounds the opening on all sides for facilitating a connection between said male and female connector units through the opening in the tab, and said connector units are secured to said tab during use with a conductive portion of one of said connector units extending through said opening in the tab, whereby said connector units provide a removable mechanical and an electrical connection to said electrode at the opening in the tab, at least one of said connector units includes a projection thereon extending through the opening in the tab and the other of said connector units is secured to said projection, one of the connector units is conductively secured to the end of the lead, a non-electrically conductive tether securing the other of said connector units to the lead, said connector units being positioned on opposite sides of the tab and being secured together with a releasable mechanical connection between the projection and one of the connector units, the lower surface of the tab is electrically conductive, one of the connector units rests in contact with said conductive lower surface and is conductively connected to the lead by means of the projection extending through the opening.

2. The biomedical electrode and electrical connector of claim 1 wherein the male and female connector units are snap connectors adapted to be united with one another by means of a snap connection and the connector units are snapped together through said opening.

3. The biomedical electrode and electrical connector of claim 1 wherein the opening comprises a plurality of intersecting cuts providing an X configuration extending through the tab from said top surface of the tab to said bottom surface thereof.

4. The biomedical electrode and electrical connection of claim 3 wherein two intersecting cuts are provided defining the opening of the tab.

5. The biomedical electrode and electrical connector of claim 1 wherein said gel matrix is on a lower surface thereof, the gel matrix has an edge defining the perimeter thereof, the tab extends laterally beyond the perimeter of the gel matrix whereby the opening in the tab extends through the tab but not through the gel matrix.

6. The biomedical electrode and electrical connector of claim 5 wherein the opening comprises a plurality of intersecting cuts extending through the tab.

7. A biomedical electrode and removable electrical connector including male and female connector units adapted to be releasably connected together and a lead wired to one of the connector units, said electrode comprising, an upper electrically insulating sheet, a lower electrically conductive layer bonded to a lower surface of the insulating sheet and a flexible electrically conductive hydrogel matrix connected to a lower surface of the electrically conductive layer and adapted to make electrically conductive contact with the skin and to conform to the body contours, a tab having a top and bottom surface and comprising superimposed layers of the insulating sheet and the electrically conductive layer, said tab having an opening therethrough from said top surface to said bottom surface for facilitating a connection between said male and female connector units through the opening in the tab, the conductive layer surrounds the opening on all sides, and said connector units are secured to said tab during use with a conductive portion of one of said connector units extending through said opening the tab, whereby said connector units provide a removable mechanical and an electrical connection to said electrode at the opening in the tab, at least one of said connector units includes a projection thereon extending through the opening in the tab and the other of said connector units is secured to said projection, one of the connector units is conductively secured to the end of the lead, a non-electrically conductive tether securing the other of said connector units to the lead, said connector units being positioned on opposite sides of the tab and being secured together with a releasable mechanical connection between the projection and one of the connector units, the lower surface of the tab is electrically conductive, one of the connector units rests in contact with said conductive lower surface and is conductively connected to the lead by means of the projection extending through the opening.

* * * * *

UNITED STATES PATENT AND TRADEMARK OFFICE
CERTIFICATE OF CORRECTION

PATENT NO. : 4,974,594

DATED : December 4, 1990

INVENTOR(S) : Lee Berlin, et al

It is certified that error appears in the above-identified patent and that said Letters Patent is hereby corrected as shown below:

Column 1, line 52, change "an" to ---and---.

Column 3, line 2, after "required", insert a ---.---.

Column 3, line 11, after "foil", insert a ---.---.

Column 3, line 14, after "patient", insert a ---.---.

On the title page, item [75], following "Inventor: Lee M. Berlin, Minnetonka, Minn.", insert -- and David Rolf, Minneapolis, Minn.--.

Signed and Sealed this

Nineteenth Day of January, 1993

Attest:

DOUGLAS B. COMER

*Attesting Officer*  *Acting Commissioner of Patents and Trademarks*